(12) United States Patent
Pesso

(10) Patent No.: US 8,574,641 B2
(45) Date of Patent: Nov. 5, 2013

(54) PEDICULICIDE COMPOSITIONS

(75) Inventor: Josef Pesso, Holon (IL)

(73) Assignee: Fischer Pharmaceuticals Ltd., Bnei Brak (IL)

( * ) Notice: Subject to any disclaimer, the term of this patent is extended or adjusted under 35 U.S.C. 154(b) by 276 days.

(21) Appl. No.: 12/994,776

(22) PCT Filed: May 21, 2009

(86) PCT No.: PCT/IL2009/000506
§ 371 (c)(1),
(2), (4) Date: Nov. 26, 2010

(87) PCT Pub. No.: WO2009/144712
PCT Pub. Date: Dec. 3, 2009

(65) Prior Publication Data
US 2011/0070323 A1 Mar. 24, 2011

(30) Foreign Application Priority Data
May 27, 2008 (IL) .......................................... 191743

(51) Int. Cl.
*A61K 36/58* (2006.01)
(52) U.S. Cl.
USPC ........................................................ 424/761
(58) Field of Classification Search
None
See application file for complete search history.

(56) References Cited

U.S. PATENT DOCUMENTS

| 6,342,253 | B1 | 1/2002 | Whitledge | |
|---|---|---|---|---|
| 2003/0027792 | A1* | 2/2003 | Ansell | 514/63 |
| 2006/0182775 | A1* | 8/2006 | Everett | 424/405 |
| 2007/0264297 | A1* | 11/2007 | Scialdone et al. | 424/405 |

FOREIGN PATENT DOCUMENTS

| EP | 1055367 A1 * | 11/2000 |
| EP | 1 512 409 | 10/2009 |
| GB | 2 341 091 | 3/2000 |
| JP | 11349424 A * | 12/1999 |
| JP | 2004099535 A * | 4/2004 |
| WO | 00/00213 | 1/2000 |

OTHER PUBLICATIONS

Priestley C M et al: "Lethality of essential . . . eggs", Fitoterapia, IDB Holding, Milan IT, vol. 77, No. 4, Jun. 1, 2006, pp. 303-309, XP024925930.
Canyon Deon V et al: "A comparison of botanical . . . infestation.", Int'l Journal of Dermatology Apr. 2007, vol. 46, No. 4, pp. 422-426, XP002567769.
International Preliminary Report on Patentability for PCT/IL2009/000506—6 pages, mailed Nov. 30, 2010.

* cited by examiner

*Primary Examiner* — Amy L Clark
(74) *Attorney, Agent, or Firm* — Roach Brown McCarthy & Gruber, P.C.; Kevin D. McCarthy

(57) ABSTRACT

A non-toxic, highly effective composition for the elimination of lice and their eggs is provided. The composition contains natural products, namely plant oils, beside harmless cosmetic additives.

6 Claims, No Drawings

PEDICULICIDE COMPOSITIONS

REFERENCE TO CO-PENDING APPLICATIONS

Priority is claimed as a 371 of international application number PCT/IL2009/000506, filed on May 21, 2009, which claims priority to Israeli patent application serial number 191743, filed on May 27, 2008.

FIELD OF THE INVENTION

The present invention relates to compositions and a method employing natural components for killing lice and their eggs.

BACKGROUND OF THE INVENTION

Head lice infestation is a widespread problem. Head lice infest a new host by close contact between individuals, making social contacts among children and parent-child interactions more likely routes of infestation than shared combs, brushes, towels, clothing, beds or closets. Head-to-head contact is by far the most common route of lice transmission. Children between 4 and 13 years of age are the most frequently infested group.

Humans are hosts of three different kinds of lice: head lice, body lice and pubic lice. The head lice (*Pediculus humanus capitis*) are wingless insects that spend their entire life on human scalp and feed exclusively on human blood. Humans are the only known host of this parasite.

The life cycle of the head lice includes three stages: egg, nymph and mature louse. Louse eggs are generally laid within 1 cm of the scalp surface, and attached to the hair by glue secreted by the adult female. A viable egg hatches to the first nymphal stage six to nine days after oviposition, and after three moltings develops to nymph 2, nymph 3 and eventually, after ten days, it matures to either a male or a female louse. The females lay an average of 3-4 eggs daily, and a generation lasts for about four weeks.

Traditionally, head lice infestations have been treated by applying kerosene on the infected hair, but this practice is painful and potentially very dangerous. Another method of prevention, especially among children, includes shaving the hair or cutting it very short, however, this method is not recommended nowadays due to possible psychological damage to the child.

Commercially available pediculicides used for topical treatment of head lice include organochlorines (lindane, DDT), organophosphates (malathion), carbamates (carbaryl), pyrethrins (pyrethrum), and pyrethroids (permethrin, phenothrin, bio-allethrin). Nevertheless, these pediculicides may rapidly lose their efficacy because of the development of resistant lice.

Natural products tested clinically and found to be safe and effective could be very important in the control of head lice, as the complexity of the active ingredients may prevent the rapid development of resistance. The natural products are more acceptable to consumers who may be concerned with the dangers of the use of chemical pediculicides. Several plant products such as aniseed, coconut, neem and tea tree oils are used in different available compositions for the treatment of head lice infestation. For example, EP 1 512 409 describes the treatment of head lice and their eggs by a composition comprising at least one essential oil, dried peppermint leaves, a tea and garlic. GB 2 341 091 discloses a formulation for treating head lice comprising a combination of tea tree oil, lavender oil and eucalyptus oil. U.S. Pat. No. 6,342,253 combines anise oil, tea tree oil and lemon oil for repelling head lice.

However, the European Cosmetic Toiletry and Perfumery Association, COLIPA, published in Recommendation No. 12 of December 2002 that tea tree oil should not be used in cosmetic products in a way that results in a concentration greater than 1% tea tree oil being applied to the body.

There is still a need for the development of new effective compositions for the treatment of lice because of the following reasons:
1. most of the available pediculicide formulations kill only the lice, while the eggs remain unaffected and continue to hatch. Hence, the researcher's approach is directed towards the development of compositions that kill not only lice, but also their eggs;
2. some pediculicides have to be applied on the head for long periods of time, which leads to compliance problems, especially with children;
3. some compositions cause irritation or sting, or may cause other inconveniences to the user;
4. several available natural formulations contain relatively high concentrations of tea tree oil, which may cause irritation.

It is therefore an object of the present invention to provide a non-toxic composition for the elimination of lice and their eggs.

It is another object of the invention to provide a composition that is highly effective in killing lice and their eggs.

Other objects of the invention will become apparent as the description proceeds.

SUMMARY OF THE INVENTION

In one aspect the invention relates to a pediculicidal composition for killing both lice and their eggs, comprising a mixture of tea tree oil, geranium oil, neem oil, andiroba oil, rosemary oil and lemongrass oil, characterized in that the composition is diluted in a solvent composition comprising SD alcohol 40, diethylhexyl adipate, cyclopentasiloxane, and dimethicone.

According to a preferred embodiment of the invention the composition comprises 0.1-3% tea tree oil, 0.5-4% geranium oil, 0.3-3% neem oil, 0.1-2% andiroba oil, 0.5-3.5% rosemary oil, 0.8-4% lemongrass oil, 8-12% SD alcohol 40, 4.5-6% diethylhexyl adipate, 45.5-58.2% cyclopentasiloxane and 25-32% dimethicone.

A preferred composition according to the invention comprises about 1% tea tree oil, about 1% geranium oil, about 1% neem oil, about 1% andiroba oil, about 1% rosemary oil, about 1% lemongrass oil, about 10% SD alcohol 40, about 5% diethylhexyl adipate, about 50% cyclopentasiloxane and about 28% dimethicone.

The invention also encompasses a method for killing lice and their eggs, comprising applying to a subject suffering from lice infestation a topical composition consisting of a mixture of tea tree oil, geranium oil, neem oil, diethylhexyl adipate, andiroba oil, rosemary oil and lemongrass oil, SD alcohol 40, cyclopentasiloxane and dimethicone.

DETAILED DESCRIPTION OF THE INVENTION

The present invention provides a composition for the elimination of lice and their eggs, comprising specific combinations of essential oils and carrier fluids, and a method for using the same.

The term "essential oil" as used herein refers to a hydrophobic liquid containing volatile aroma compound derived from a plant. The term "carrier fluid" as used herein refers to a solvent in which the essential oils of the present invention are diluted. These fluids can be, for instance, alcohols such as ethanol, polyols such as glycerol, non-essential oils and silicones such as cyclopentasiloxane and dimethicone.

It has now been surprisingly found that certain combinations of essential oils comprising tea tree oil, geranium oil, neem oil, andiroba oil, rosemary oil and lemongrass oil, when diluted in a solvent comprising SD alcohol 40, diethylhexyl adipate, cyclopentasiloxane and dimethicone, are extremely effective in killing lice and their eggs. The resulted pediculicide, provided in the present invention, is based on natural products, non-toxic, and mild.

Preferably, the pediculicidal composition comprises essential oils in the following amounts: 0.1-5% tea tree oil and more preferably 0.1-3%, 0.5-4% geranium oil, 0.3-3% neem oil, 0.1-2% andiroba oil, 0.5-3.5% rosemary oil and 0.8-4% lemongrass oil.

Unless otherwise indicated, all percentages given herein are by weight and based on the total composition.

Preferably, the pediculicidal composition comprises carrier fluids in the following amounts: 8-12% SD alcohol 40, 4.5-6% diethylhexyl adipate 45.5-58.2% cyclopentasiloxane and 25-32% dimethicone.

More Preferably, the composition of the present invention comprises about 1% tea tree oil, about 1% geranium oil, about 1% neem oil, about 1% andiroba oil, about 1% rosemary oil, about 1% lemongrass oil, about 10% SD alcohol 40, about 5% diethylhexyl adipate, about 50% cyclopentasiloxane and about 28% dimethicone.

According to one aspect of the invention, the pediculicidal composition can be safely applied to the skin, hair and scalp of adults and children over three years old, for up to 15 minutes.

The pediculicidal composition of the present invention may be provided in various forms, for instance, in the form of a shampoo, a conditioner, a gel, a spray, and a cream. According to the preferred embodiment, the composition is in the form of oil in spray without gas.

The invention will be further described and illustrated in the following examples.

EXAMPLES

Safety Assessment

A preferred composition comprising 1% tea tree oil, 1% geranium oil, 1% neem oil, 1% andiroba oil, 1% rosemary oil, 2% lemongrass oil, 13% SD alcohol 40, 5% diethylhexyl adipate, 47% cyclopentasiloxane and 28% dimethicone was evaluated for the exposure risk for consumers. The composition was found to be in conformity with the requirements of the French Decree 2000-569 of 23 Jun. 2000 and to the Code of Sante Publique Art R-5131-2 and 3 Section I and II as in the Cosmetic European Directive 76/769, 93/95 and 2003/15 modified, and not likely to harm health when used under the normal conditions.

General Procedures

All formulations described hereinafter were tested for their pediculicidal and ovicidal activity under laboratory conditions, according to the following procedures:

1. Protocol for lice: Body lice (*Pediculus humanus humanus*) are reared in the laboratory according to the method described by Cole (Cole, M. M. 1966. Body lice. In: Insect colonization and mass production. Smith, C. N. (ed.), Academic Press, N. York, p. 15-24). For each test, 50 lice (10 males, 10 females and 30 nymphs) were placed on a 7-cm white filter paper disc and exposed to 1 g of the test formulation. The lice were left in contact with the substance for 15 min. They were removed from the filter paper, washed with normal shampoo (1:20) for 1 min and then with tap water for 1 min. After treatment, lice were transferred to a fresh filter paper disc and incubated overnight at optimum temperature and humidity. Mortality was determined after 24 hours.

2. Protocol for eggs: Lice were placed on human hair every other day for 5 days and left for 24-48 hours for oviposition. Fifty eggs, 2-6 days old were treated the same way as lice. The number of hatched and non-hatched eggs was counted after 10 days.

As a negative control, lice treated with 40% ethyl alcohol, were used. Each formulation was tested in triplicate.

The Cole method uses body lice rather than head lice since head lice are not successfully reared in the laboratory.

The essential oils comprising the formulations of the invention are referred to herein according to their trade name, while the carrier fluids are used by their INCI name. Table 1 presents the different ingredients of the formulations by their trade name, INCI name, CAS name, manufacturer and Catalog No. of the manufacturer.

TABLE 1

| Trade name | INCI Name | CAS No. | Manufacturer | Catalog No. (Manufacturer) |
|---|---|---|---|---|
| Tea tree oil | *Melaleuca alternifolia* (Tea Tree) leaf oil | 68647-73-4 | Dullberg | 744-125 |
| Geranium oil | *Pelargonium graveolens* Flower oil | 8000-46-2 | Citrus and allied | 21150 |
| Neem oil | *Melia azadirachta* seed oil | 68956-68-7 | Dullberg | 741-525 |
| Crodamol DOA | Diethylhexyl adipate | 103-23-1 | Croda | DS03781/ 0190/M95 |
| Andiroba oil | *Carapa guaianensis* seed oil | 352458-32-3 | Beraca | RF3110 |
| Rosemary oil | *Rosmarinus officinalis* (Rosemary) leaf oil | 8000-25-7 | Citrus and allied | 4223 |
| Lemongrass oil | *Cymbopogon schoenanthus* oil | 8007-02-1 | Citrus and allied | C: 5520 |
| Ethanol SDA 40 | SD Alcohol 40 | 64-17-15 | Gadot | 810113996 |
| Silicone volatile 245 | Cyclopentasiloxane | 541-02-6 | Momentive | 7390 SF 1202 |
| Silicone oil 200/350 | Dimethicone | 9006-65-9; 63148-62-9; 9016-00-6; | Momentive | 6408 Oil M 350 |

Example 1

Formulation samples A-J as well as a composition according to the invention, identified as P-782, all containing different concentrations of essential oils diluted in different carrier fluids, were prepared and tested for their pediculicidal and ovicidal activity.

TABLE 2

|  | A | B | C | D | E | F | G | H | I | J | P-782 |
|---|---|---|---|---|---|---|---|---|---|---|---|
| Tea tree oil | 10 | 5 | 10 | 5 | 5 | 1 | 1 | 1 | 1 | 1 | 1 |
| Geranium oil | 2 | 5 | 5 | 5 | 5 | 5 | 1 | 5 | 1 | 5 | 1 |
| Neem oil | 3 | 3 | 3 | 3 | 3 | 3 | 3 | 1 | 1 | 3 | 1 |
| Diethylhexyl adipate | — | — | — | 16 | 5 | 5 | 5 | 5 | 5 | — | 5 |
| Andiroba oil | 1 | 1 | 1 | 1 | 1 | 1 | 1 | 1 | 1 | 1 | 1 |
| Rosemary oil | 1 | 1 | 1 | 1 | 1 | 1 | 1 | 1 | 1 | 1 | 1 |
| Lemongrass oil | 3 | 2 | 2 | 2 | 2 | 2 | 1 | 2 | 2 | 2 | 1 |
| Eutanol G | 80 | 83 | 78 | — | — | — | — | — | — | — | — |
| SD Alcohol 40 | — | — | — | 8.3 | 9.5 | 10 | 10.5 | 10.5 | 10.7 | 10.6 | 10.7 |
| Cyclopentasiloxane | — | — | — | 37.7 | 44 | 46 | 49 | 47.1 | 49.4 | 48.8 | 49.9 |
| Dimethicone | — | — | — | 21 | 24.5 | 26 | 27.5 | 26.4 | 27.9 | 27.6 | 28.4 |
| Lice Mortality % | 54 | 63 | 23 | 100 | 100 | 100 | 100 | 100 | 100 | 100 | 100 |
| Egg Mortality % | 31 | 41 | 27 | 73 | 91 | 77 | 37 | 40 | 42 | 34 | 80 |

The test results in Table 2 show that the use of SD alcohol 40, diethylhexyl adipate, cyclopentasiloxane and dimethicone as carrier fluids (formulation samples D-N) instead of eutanol G (formulation samples A-C) significantly increases both the pediculicidal and the ovicidal activity of the composition of the invention. Moreover, the results of the lice and egg mortality clearly demonstrate that samples D-N killed 100% of the lice, yet affected the eggs in different percentages. This fact indicates that fine tuning of the different ingredients comprising the formulations is required in order to achieve maximal ovicidal efficiency. Formulation E, which exhibited the highest egg mortality (91%), was not chosen to be the final composition due to the relatively high total concentration of essential oils in it. The composition according to the present invention, formulation P-782, killed 100% of the lice and 80% of the eggs.

The pediculicidal and ovicidal effect of P-782 on lice and their eggs was further tested 5, 10 and 15 minutes after treatment. The formulation rapidly killed the lice, and even after 5 minutes of exposure, they exhibited a mortality rate of 100%. Nevertheless, the elimination of 80% of the eggs required their exposure to P-782 for 15 minutes.

Example 2

The efficacy of composition P-782 of Example 1 in killing lice and their eggs was compared with two commercially available pediculicides, soled under the trade names Finale and Chick Chack. Finale is a natural tea tree oil spray, comprising 10% tea tree oil, rosemary oil, lavender oil, eucalyptus oil, mentha oil, geranium oil, and tocopheryl acetate, manufactured by NSP, Hadera, Israel. This formulation exceeds by ten fold COLIPA recommendations regarding tea tree oil concentrations. Chick Chack is a natural composition rich in essential oils, which contains coconut oil, anise oil, Ylang-Ylang oil and isopropyl alcohol, manufactured by CST NOVIS, Kiryat Malachi, Israel.

TABLE 3

|  | Finale | Chick Chack | P-782 |
|---|---|---|---|
| Lice mean % mortality | 62 | 100 | 100 |
| Eggs mean % mortality | 14 | 55-59 | 80 |

Table 3 shows that Finale poorly succeeded in killing both lice and their eggs. Although P-782 and Chick Chack eliminated all lice, Chick Chack was much less efficient than P-782 in killing the eggs: Therefore, the specific formulation of the present invention is clearly superior to compositions currently available on the market.

Example 3

The composition of Example 1 in the form of a spray is applied to an individual suffering from head lice in the following manner:
1. Spray the lotion over dry hair and scalp;
2. Leave the lotion on for 15 minutes;
3. Wash the hair with regular shampoo to remove the lotion;
4. Repeat steps 1-3 after 10 days.

Example 4

A sensation test for formulation P-782 was carried out on 20 children between the ages 8 and 12 by their mothers (the average age being 10). The composition was applied to the dry hair and scalp of the subjects, remained for 15 minutes and was then washed off with the subject's regular shampoo. The procedure was repeated after seven days. Only 10-15% of the mothers reported irritation occurrences during the application of the composition and the 15 minutes wait, and one subject reported a singe in the eye area. 80% of the mothers were satisfied with the feeling sensation and the ease of use of the composition.

Example 5

A sensation test for composition P-782 was carried out on 21 women of age 20 years and up. The composition was applied to the dry hair and scalp of the subjects, remained for 15 minutes and was then washed off with the subject's regular shampoo. The procedure was repeated after seven days. 19% of the women reported irritation occurrences during the application of the composition and the 15 minutes wait, and 14% reported slight burning sensation in the eye area. Most of the subjects were satisfied with the feeling sensation and the ease of use of the composition.

While this invention has been described in terms of some specific examples, many modifications and variations are possible. It is therefore understood that within the scope of the appended claims, the invention may be carried out in a manner different from that specifically described.

The invention claimed is:
1. A pediculicidal composition for killing lice and lice eggs, consisting of an effective amount of tea tree oil, geranium oil, neem oil, andiroba oil, rosemary oil, lemongrass oil,

SD alcohol 40, diethylhexyl adipate, cyclopentasiloxane, and dimethicone, wherein the composition is safely applied to the skin, hair and scalp of adults and children.

2. The composition of claim 1, wherein the composition consists of tea tree oil in an amount of 0.1-3%, geranium oil in an amount of 0.5-4%, neem oil in an amount of 0.03-3%, andiroba oil in an amount of 0.1-2%, rosemary oil in an amount of 0.5-3.5%, lemongrass oil in an amount of 0.8-4%, SD alcohol 40 in an amount of 8-12%, diethylhexyl adipate in an amount of 4.5-6%, cyclopentasiloxane in an amount of 45.5-58.2% and dimethicone in an amount of 25-32%.

3. The composition of claim 1, wherein the composition consists of tea tree oil in an amount of about 1%, geranium oil in an amount of about 1%, neem oil in an amount of about 1%, andiroba oil in an amount of about 1%, rosemary oil in an amount of about 1%, lemongrass oil in an amount of about 1%, SD alcohol 40 in an amount of about 10%, diethylhexyl adipate in an amount of about 5%, cyclopentasiloxane in an amount of about 50% and dimethicone in an amount of about 28%.

4. A method for killing lice and lice eggs on a subject in need thereof, comprising topically applying to skin, hair and/or scalp of said subject a composition consisting of an effective amount of tea tree oil, geranium oil, neem oil, andiroba oil, rosemary oil, lemongrass oil, SD alcohol 40, diethylhexyl adipate, cyclopentasiloxane and dimethicone, wherein the composition is safe for application to the skin, hair and scalp of adults and children.

5. The method of claim 4, wherein the composition consists of tea tree oil in an amount of 0.1 -3%, geranium oil in an amount of 0.5-4%, neem oil in an amount of 0.03-3%, androba oil in an amount of 0.1-2%, rosemary oil in an amount of 0.5-3.5%, lemongrass oil in an amount of 0.8-4%, SD alcohol 40 in an amount of 8-12%, diethylhexyl adipate in an amount of 4.5-6%, cyclopentasiloxane in an amount of 45.5-58.2% and dimethicone in an amount of 25-32%.

6. The method of claim 4, wherein the composition consists of tea tree oil in an amount of about 1%, geranium oil in an amount of about 1%, neem oil in an amount of about 1%, andiroba oil in an amount of about 1%, rosemary oil in an amount of about 1%, lemongrass oil in an amount of about 1%, SD alcohol 40 in an amount of about 10%, diethylhexyl adipate in an amount of about 5%, cyclopentasiloxane in an amount of about 50% and dimethicone in an amount of about 28%.

* * * * *